United States Patent
Robles et al.

(10) Patent No.: US 11,650,149 B2
(45) Date of Patent: May 16, 2023

(54) CELL IMAGING SYSTEMS AND METHODS

(71) Applicant: Georgia Tech Research Corporation, Atlanta, GA (US)

(72) Inventors: Francisco Robles, Atlanta, GA (US); Patrick Ledwig, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 407 days.

(21) Appl. No.: 17/040,647

(22) PCT Filed: Mar. 26, 2019

(86) PCT No.: PCT/US2019/024025
§ 371 (c)(1),
(2) Date: Sep. 23, 2020

(87) PCT Pub. No.: WO2019/191061
PCT Pub. Date: Oct. 3, 2019

(65) Prior Publication Data
US 2021/0025818 A1    Jan. 28, 2021

Related U.S. Application Data

(60) Provisional application No. 62/648,180, filed on Mar. 26, 2018.

(51) Int. Cl.
*G01N 21/41*      (2006.01)
*G01N 33/483*    (2006.01)
(Continued)

(52) U.S. Cl.
CPC ......... *G01N 21/41* (2013.01); *G01N 33/4833* (2013.01); *G02B 21/06* (2013.01);
(Continued)

(58) Field of Classification Search
CPC ............... G01N 21/41; G01N 33/4833; G01N 2021/418; G01N 2201/062;
(Continued)

(56) References Cited

U.S. PATENT DOCUMENTS

2013/0130307 A1*   5/2013  Sugiyama .............. G01N 21/45
                                                                    435/288.7
2013/0288286 A1   10/2013  Sugiyama et al.
(Continued)

OTHER PUBLICATIONS

Search Report and Written Opinion from Application No. PCT/US2019/024025 dated Jun. 14, 2019 (7 pages).

*Primary Examiner* — Sang H Nguyen
(74) *Attorney, Agent, or Firm* — Troutman Pepper Hamilton Sanders LLP; Ryan A. Schneider; Nicholas Doss

(57) ABSTRACT

Disclosed herein are systems and methods for imaging cells. Quantitative phase imaging uses variations in the index of refraction of a sample as a source of endogenous contrast, providing label-free information of sub-cellular structures and allowing for the reconstruction of valuable biophysical parameters, such as cell dry-mass at femtogram scales, mass transport, and sample thickness and fluctuations at nanometer scales. As a result, QPI has become a valuable tool in biology and medicine. However, QPI has suffered from the need for trans-illumination through relatively thin objects in order to gain access to the forward-scattered field, which carries crucial low spatial frequency information of a sample and avoid contributions from multiple scattered light or out-of-focus planes. The disclosed methods and systems can provide for reconstruction of QPI and corresponding analysis for imaging samples of cells in thick samples using an epi-illumination configuration.

22 Claims, 11 Drawing Sheets

(51) Int. Cl.
  *G02B 21/36* (2006.01)
  *G02B 21/06* (2006.01)
  *G06K 9/00* (2022.01)
  *G06V 20/69* (2022.01)

(52) U.S. Cl.
  CPC ......... *G02B 21/365* (2013.01); *G06V 20/693* (2022.01); *G06V 20/698* (2022.01); *G01N 2021/418* (2013.01); *G01N 2201/061* (2013.01); *G01N 2201/062* (2013.01); *G01N 2201/0826* (2013.01)

(58) Field of Classification Search
  CPC ..... G01N 2201/0826; G01N 2201/061; G02B 21/365; G02B 21/06; G06V 20/698; G06V 20/693
  See application file for complete search history.

(56) References Cited

U.S. PATENT DOCUMENTS

| | | |
|---|---|---|
| 2013/0335548 A1 | 12/2013 | Kim et al. |
| 2015/0100278 A1 | 4/2015 | Gaylord et al. |
| 2015/0185460 A1 | 7/2015 | Nakasho et al. |
| 2016/0252719 A1* | 9/2016 | Liu .................... G01N 33/4833 348/49 |
| 2016/0300341 A1 | 10/2016 | Hay et al. |
| 2018/0286038 A1* | 10/2018 | Jalali ..................... G06N 3/086 |

* cited by examiner

CELL IMAGING SYSTEMS AND METHODS

CROSS-REFERENCE TO RELATED APPLICATIONS

This application claims the benefit, under 35 U.S.C. § 119(e), of U.S. Provisional Patent Application No. 62/648,180, filed 26 Mar. 2018, the entire contents and substance of which is incorporated herein by reference in its entirety as if fully set forth below.

FIELD OF THE DISCLOSURE

The present disclosure relates generally to cell imaging systems and methods. Particularly, embodiments of the present disclosure relate to multi-wavelength and/or quantitative oblique back-illumination microscopy.

BACKGROUND

Quantitative Phase Imaging ("QPI") uses variations in the index of refraction of a sample as a source of endogenous contrast, providing label-free information of sub-cellular structures and allowing for the reconstruction of valuable biophysical parameters, such as cell dry-mass at femtogram scales, mass transport, and sample thickness and fluctuations at nanometer scales. As a result, QPI has become a valuable tool in biology and medicine, with a growing set of applications in fields like oncology, hematology, pathology, immunology, developmental biology, and neuroscience. However, QPI has suffered from the need for trans-illumination through relatively thin objects in order to gain access to the forward-scattered field, which carries crucial low spatial frequency information of a sample and avoid contributions from multiple scattered light or out-of-focus planes. This restriction has severely limited the biological applicability of phase imaging to mostly thinly-sliced histological tissue, cultured cells, or thin transparent samples in-vitro.

Methods for QPI typically involve interfering beams of a coherent source, but phase contrast itself can be produced simply with partially coherent asymmetric illumination in a typical wide-field microscope, without interferometry. Images produced from incoherent or partially coherent light sources have the advantage of increased resolution and a lack of noise from speckle or other coherent artifacts. Improved methods of QPI have potential to greatly expand the design space and capabilities of certain practices, such as stem cell characterization, stem cell therapy, transplant tissue characterization, white blood cell count, storage lesions, endoscopy, in-vivo imaging and the like.

What is needed, therefore, is an improved cell imaging technique to enable a rich level of quantitative detail in thick scattering samples similar to that achieved with thin forward-illuminating samples. Embodiments of the present disclosure address this need as well as other needs that will become apparent upon reading the description below in conjunction with the drawings.

BRIEF SUMMARY OF THE INVENTION

The present invention relates to cell imaging systems and methods. An exemplary embodiment of the present invention provides a method of imaging cell samples, comprising: obtaining a quantitative phase image of a plurality of cells; obtaining a distribution of light frequency absorption data for the plurality of cells; cross-correlating a sample model of a desired cell with the quantitative phase image to compare each cell from the plurality of cells with the sample model of the desired cell; indicating at least one cell from the plurality of cells similar to the sample model as a first desired cell candidate; indicating at least one cell from the plurality of cells having a light frequency absorption outside of a threshold standard deviation from the plurality of cells as a second desired cell candidate; and determining, based on the quantitative phase image and the distribution of light frequency absorption data, if the first desired cell candidate and the second desired cell candidate are the same cell.

In any of the embodiments disclosed herein, obtaining a distribution of light frequency absorption data can comprise: illuminating the plurality of cells with light at a first frequency; illuminating the plurality of cells with light at a second frequency; and receiving two or more illuminated images of the plurality of cells.

In any of the embodiments disclosed herein, the method can further comprise comparing a value of light absorbed at the first frequency to light absorbed at the second frequency for each cell from the plurality of cells.

In any of the embodiments disclosed herein, the method can further comprise constructing a phase gradient image by subtracting an illuminated image at the second frequency from an illuminated image at the first frequency.

In any of the embodiments disclosed herein, the method can further comprise constructing an absorption contrast image by adding the two or more illuminated images together.

In any of the embodiments disclosed herein, the illuminating can comprise: emitting light at the first frequency from a first pair of light sources; and emitting light at the second frequency from a second pair of light sources. The first and second pairs of light sources and an objective lens can be on a same side of the plurality of cells. The first and second pairs of light sources can be configured to transmit light obliquely to the plurality of cells.

In any of the embodiments disclosed herein, the first and second light sources can comprise two or more light-emitting devices.

In any of the embodiments disclosed herein, the two or more light-emitting devices can comprise light-emitting diodes (LEDs).

In any of the embodiments disclosed herein, the two or more light-emitting devices comprise fiber optic cables.

In any of the embodiments disclosed herein, a first and a second light-emitting device can be positioned flanking the objective, such that each of the first and second light sources can comprise a first and a second light-emitting device on either side of the objective.

In any of the embodiments disclosed herein, the first and the second light-emitting devices on either side of the objective can form an orthogonal angle with each other, such that each of the first and second light sources comprise a first and a second light-emitting device on either side of the objective and forming an orthogonal angle.

In any of the embodiments disclosed herein, the method can further comprise labelling the cell corresponding to the first and the second desired cell candidate as a desired cell, responsive to determining that the first and second desired cell candidates are the same cell.

In any of the embodiments disclosed herein, the method can further comprise labelling the cell corresponding to the first and the second desired cell candidate as a false positive, responsive to determining that the first and second desired cell candidates are not the same cell.

In any of the embodiments disclosed herein, the indicating at least one cell from the plurality of cells having a light frequency absorption outside of a threshold standard deviation from the plurality of cells can comprise: illuminating the plurality of cells with light at a first frequency; illuminating the plurality of cells with light at a second frequency; calculating the ratio of light absorbed at the first frequency to light absorbed at the second frequency for each cell from the plurality of cells; and determining which cells from the plurality of cells have a ratio of light absorbed outside a threshold standard deviation value from the plurality of cells.

In any of the embodiments disclosed herein, the desired cell can be a white blood cell.

In any of the embodiments disclosed herein, the plurality of cells can comprise blood cells.

In any of the embodiments disclosed herein, the cells can be obtained from any organ or organoid belonging to a living organism.

Another embodiment provides a method of imaging blood comprising: illuminating a plurality of blood cells with light at a first frequency from a first light source; illuminating the plurality of blood cells with light at a second frequency from a second light source; receiving two or more illuminated images of the plurality of blood cells at an objective; constructing a quantitative phase image from the two or more illuminated images with epi illumination by including the two or more illuminated images together; cross-correlating a sample model of a white blood cell with the quantitative phase image to compare each cell from the plurality of blood cells with the white blood cell; indicating at least one cell from the plurality of blood cells matches the sample model as a first white blood cell candidate; indicating at least one cell from the plurality of blood cells having a light frequency absorption ratio outside of a threshold standard deviation from the plurality of cells as a second white blood cell candidate; determining, based on the quantitative phase image and the distribution of light frequency absorption data, if the first white blood cell candidate and the second white blood cell candidate are the same cell; and labelling the cell corresponding to the first and the second white blood cell candidate as a white blood cell, responsive to determining that the first and second white blood cell candidates are the same cell.

Another embodiment provides a method of imaging cell samples, comprising: cross-correlating a sample model of a desired cell with a quantitative phase image to compare each cell from a plurality of cells with the desired cell; indicating at least one cell from the plurality of cells similar to the sample model as a first desired cell candidate; indicating at least one cell from the plurality of cells having a light frequency absorption outside of a threshold standard deviation from the plurality of cells as a second desired cell candidate; and determining, based on the quantitative phase image and the distribution of light frequency absorption data, if the first desired cell candidate and the second desired cell candidate are the same cell.

In any of the embodiments disclosed herein, the method can further comprise: obtaining a distribution of light frequency absorption data by: illuminating the plurality of cells with light at a first frequency; illuminating the plurality of cells with light at a second frequency; and receiving two or more illuminated image of the plurality of cells at an objective.

In any of the embodiments disclosed herein, the method can further comprise calculating a ratio of light absorbed at the first frequency to light absorbed at the second frequency for each cell from the plurality of cells.

Another embodiment provides a system for the imaging of cells. The system comprises a first and a second light source, an objective image-capturing device, a display, a processor, and memory. Each of the first and second light sources can comprise two or more light-emitting devices. The memory can store instructions that, when executed by the processor, cause the system to: receive imaging data from the objective image-capturing device, the imaging data comprising light frequency absorption data for a plurality of cells; construct, using the light frequency absorption data, a quantitative phase image of the plurality of cells; cross-correlate a sample model of a desired cell with the quantitative phase image to compare each cell from the plurality of cells with the sample model of the desired cell; indicate at least one cell from the plurality of cells similar to the sample model as a first desired cell candidate; indicate at least one cell from the plurality of cells having a light frequency absorption outside of a threshold standard deviation from the plurality of cells as a second desired cell candidate; and determine, based on the quantitative phase image and the distribution of light frequency absorption data, if the first desired cell candidate and the second desired cell candidate are the same cell.

In any of the embodiments disclosed herein, the at least one memory can further comprise instructions, that when executed by the processor, cause the system to: illuminate the plurality of cells with light from the first light source at a first frequency; illuminate the plurality of cells with light from the second light source at a second frequency; receive two or more illuminated images of the plurality of cells at an objective; and receive light frequency absorption data from the objective imaging device.

In any of the embodiments disclosed herein, the at least one memory can further comprise instructions, that when executed by the processor, cause the system to calculate a ratio of light absorbed at the first frequency to light absorbed at the second frequency for each cell from the plurality of cells.

In any of the embodiments disclosed herein, the at least one memory can further comprise instructions, that when executed by the processor, cause the system to construct a phase gradient image by subtracting an illuminated image at the second frequency from an illuminated image at the first frequency.

In any of the embodiments disclosed herein, the at least one memory can further comprise instructions, that when executed by the processor, cause the system to construct an absorption contrast image by adding the two or more illuminated images together.

In any of the embodiments disclosed herein, the first and second light sources can be on the same side of the plurality of cells as the objective.

In any of the embodiments disclosed herein, the first and second light sources can be configured to transmit light obliquely to the plurality of cells.

In any of the embodiments disclosed herein, the at least one memory can further comprise instructions, that when executed by the processor, cause the system to label the cell corresponding to the first and the second desired cell candidate as a desired cell, responsive to determining that the first and second desired cell candidates are the same cell.

In any of the embodiments disclosed herein, the at least one memory can further comprise instructions, that when executed by the processor, cause the system to transmit the imaging data to the display.

In any of the embodiments disclosed herein, the at least one memory further comprises instructions, that when executed by the processor, cause the system to transmit at least one image from the two or more illuminated images of the plurality of cells to the display.

In any of the embodiments disclosed herein, the at least one image can comprise the desired cell labels applied by the system.

In any of the embodiments disclosed herein, the at least one memory can further comprise instructions, that when executed by the processor, cause the system to label the cell corresponding to the first and the second desired cell candidate as a false positive, responsive to determining that the first and second desired cell candidates are not the same cell.

In any of the embodiments disclosed herein, the at least one memory can further comprise instructions, that when executed by the processor, cause the system to: calculate the ratio of light absorbed at the first frequency to light absorbed at the second frequency for each cell from the plurality of cells; and determine which cells from the plurality of cells have a ratio of light absorbed outside a threshold standard deviation value from the plurality of cells.

In any of the embodiments disclosed herein, the desired cell can be a white blood cell.

In any of the embodiments disclosed herein, the plurality of cells can comprise blood cells.

In any of the embodiments disclosed herein, the blood cells can be obtained from any organ or organoid belonging to a living organism.

Another embodiment provides a system for imaging cells comprising a first and a second light source, an objective image-capturing device, a plurality of cells, a process, and memory. Each of the first and second light source can comprise two or more light-emitting devices and can be configured to illuminate a plurality of cells. The memory can store instructions that, when executed by the processor, cause the system to: receive imaging data from the objective image-capturing device, the imaging data comprising light frequency absorption data for a plurality of cells; construct, using the light frequency absorption data, a quantitative phase image of the plurality of cells; cross-correlate a sample model of a desired cell with the quantitative phase image to compare each cell from the plurality of cells with the desired cell; indicate at least one cell from the plurality of cells similar to the sample model as a first desired cell candidate; indicate at least one cell from the plurality of cells having a light frequency absorption outside of a threshold standard deviation from the plurality of cells as a second desired cell candidate. The first and second light sources can be on the same side of the plurality of cells as the objective and are configured to transmit light obliquely to the plurality of cells. A first and a second light-emitting device from the two or more light-emitting devices can be positioned flanking the objective, such that each of the first and second light sources comprise a first and a second light-emitting device on either side of the objective. The first and the second light-emitting devices on either side of the objective can form an orthogonal angle with each other, such that each of the first and second light sources comprise a first and a second light-emitting device on either side of the objective and forming an orthogonal angle.

These and other aspects of the present invention are described in the Detailed Description of the Invention below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1A:
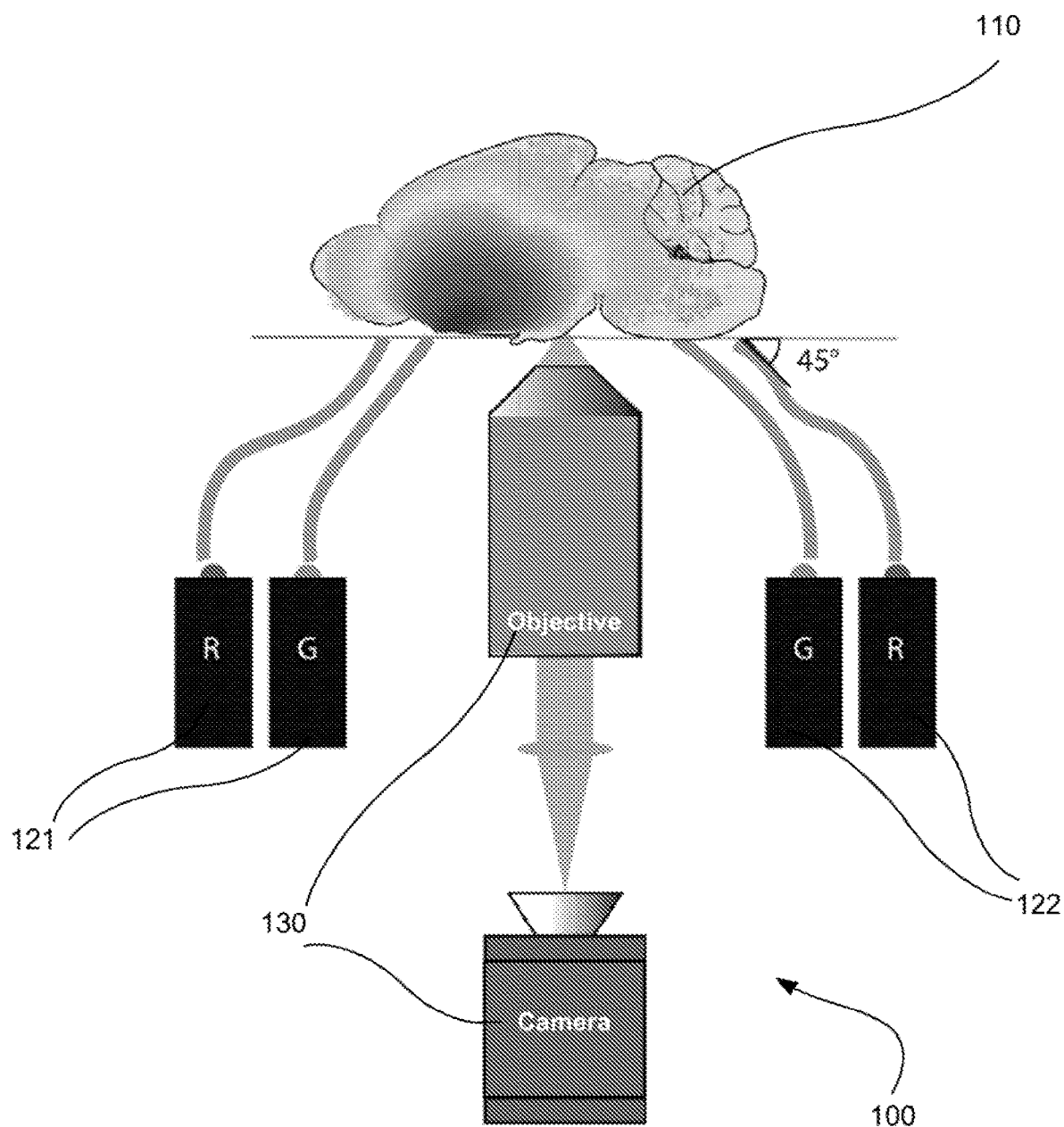
FIG. 1a illustrates an exemplary embodiment of a system for cell imaging.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

As described above, a problem with current quantitative phase imaging (QPI) techniques is the need for trans- or forward-illumination and thus, the need for a thin sample. This restriction has severely limited the biological applicability of phase imaging to mostly thinly-sliced tissue samples, cultured cells, or other transparent samples. With the design capacity for QPI techniques expanding in areas such as oncology, hematology, pathology, immunology, developmental biology, and neuroscience, improved cell imaging methods are desirable.

The field of incoherent or partially coherent light sources have been explored. Images produced from incoherent or partially coherent light sources have the advantage of increased resolution and a lack of noise from speckle or other coherent artifacts. The phase contrast produced from asymmetric illumination can be used to recover quantitative phase with a complete linearized model of the imaging system via a regularized deconvolution with the optical transfer function of the microscope. This type of phase reconstruction method does not suffer from phase wrapping artifacts and has recently been widely adopted for QPI (including 3D tomographic phase reconstruction of thin samples) using partially coherent structured illumination sources such as LED arrays and modified pupils.

Using principles of asymmetric illumination to recover quantitative phase, transmissive QPI has been transformed into an epi-mode imaging modality with tomographic capabilities. To achieve this, a modified version of an illumination scheme known as oblique back-illumination microscopy (OBM) can be used, which produces a virtual light source within a thick sample, via multiple scattering, that emulates a transmission geometry with oblique illumination. By subtracting two images acquired with opposite oblique illumination angles, this strategy effectively removes contributions from out-of-focus planes, and yields high-resolution, tomographic differential phase contrast in thick specimens. Then, the multiple scattering process used for illumination to arrive at the ensemble average angular distribution of light approaching the target can be modeled, and ultimately converted into a transfer function of the system. This allows for use of regularized deconvolution methods to recover quantitative phase. This approach, termed quantitative oblique back-illumination microscopy (qOBM), incorporates the trappings of QPI into a versatile epi-configuration, allowing non-invasive, label-free, real-time quantitative imaging in media that are otherwise out of the reach of previous QPI technologies. With qOBM, quantitative phase imaging can now be extended to many more areas of biomedicine. Disclosed herein are the system and theoretical framework of the aforementioned techniques.

Disclosed herein is a method for imaging a plurality of cells. The method can comprise imaging and deconvolution to obtain a QPI of a sample. The QPI can be obtained in a number of ways, but a method of interest utilizes oblique back-illumination microscopy. In other words, light sources on the same side of the sample as the imaging device illuminate the sample at multiple oblique angles. Such illumination can produce a virtual light source within a thick sample, via multiple scattering, that emulates a transmission geometry with oblique illumination. An image of the sample can be obtained by subtracting two or more images acquired with opposing oblique illumination angles. For example, two light sources can be placed to form an orthogonal angle with one another while remaining oblique to the sample. The subtracting effectively removes light transmission and absorption from out-of-focus planes and yields high-resolution differential phase contrast images of the area of the thick sample in question. In other words, the aforementioned strategy can image a thick sample to produce an effective cross-sectional image of the sample at a desired area. The differential phase contrast image is then processed using mathematical formulas, such as the multiple scattering process used for illumination, to obtain the average angular distribution of light received by the imaging device. This device can be used to obtain the transfer function of the system. That is, spatial data relating to locations in the spatial domain can be transferred to become frequency data in the frequency domain, as frequency data is desirable in some applications where the cells of interest absorb light at differing frequencies. From this transfer function, the differential phase contrast image can be deconvoluted to recover a quantitative phase image (QPI). Such an embodiment can provide non-invasive, label-free, and real-time quantitative imaging in media that are otherwise out of the reach of currently known QPI technologies.

Disclosed herein are systems for imaging cells. Embodiments of the present disclosure can provide a system comprising a plurality of light sources (e.g., one or more, two or more, three or more, four or more, etc.), an objective image-capturing device (such as a camera), a display, a plurality of storage devices/memory (e.g., one or more, two or more, three or more), and a plurality of processors (e.g., one or more, two or more, three or more). For instance, the system can comprise four or more light sources in the form of light-emitting diodes (LEDs) or optical fibers, and an objective camera configured to illuminate samples and capture images of samples. The imaging and illumination data can be transmitted to one or more storage devices at a computer. The one or more processors at the computer can be configured to process the images and/or the illumination data and can contain respective instructions for the processing of the data. The display can also be in communication with the computer and can receive images and/or data to display to the user from the storage devices or the processors.

Figure 1B:
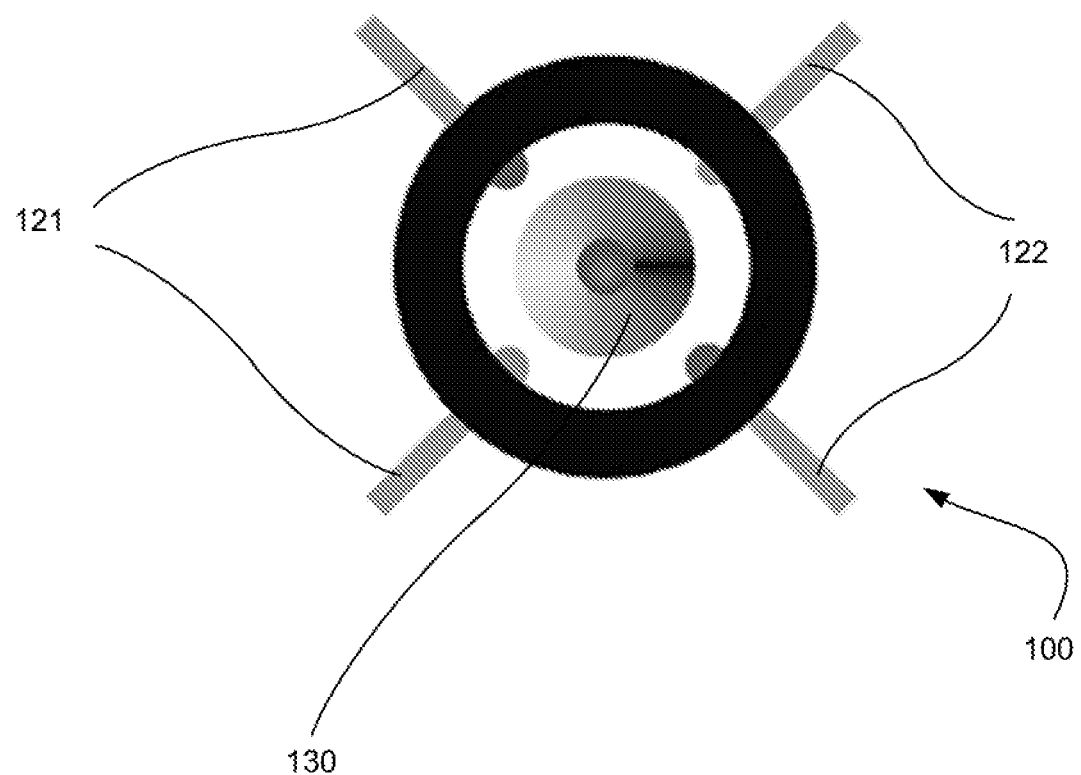
FIG. 1b illustrates an exemplary embodiment of a system for cell imaging.

For example, FIG. 1a provides an exemplary embodiment of a system for imaging cells. In some embodiments, the system consists of a traditional microscope with epi-illumination emanating from two pairs of optical fibers positioned around the objective housing. As used herein, the term "epi-illumination" refers to illumination techniques wherein the illumination light source emits from the same side of the sample as the objective image-capturing device. The fibers from each pair can be placed diametrically opposite from one another as shown in FIG. 1b. When light from an LED light source is deployed through one of the fibers, it produces trans-illumination at the focus of the microscope objective by way of multiple scattering. With an overall oblique illumination at the focal plane, lateral variations in index of refraction redirect light toward or away from the acceptance angles of the objective's numerical aperture, producing phase contrast in observed intensity. As with oblique back-illumination microscopy (OBM), quantitative oblique back-illumination microscopy (qOBM) first generates differential phase contrast by subtracting images taken with the diametrically opposed fibers. Again, the asymmetric illumination and the subtraction process produce differential phase contrast; and, as out of focus contributions in either illumination image are the same, the subtraction process rejects out of focus content, allowing for tomographic sectioning.

In some embodiments, the plurality of processors can contain instructions for processing the imaging and illumination data received from the objective image capturing device. Such data can be in the form of spatial location data, illumination absorption data, illumination transmission data, frequency data, wavelength data, and the like. In some embodiments, the plurality of processors (such as the one or more processors) can be configured to process different images to construct phase images. As mentioned above, the one or more processors can contain instructions configured to construct a differential phase contrast image (DPC) and/or a quantitative phase image (QPI), as outlined generally in FIG. 10. Constructing such images would allow for greater analysis of the imaging data received from the sample.

In practice, differential phase contrast can be produced by first normalizing each intensity image by its overall variance, which removes any variations between the LED output. Then, images corresponding to the diametrically opposed sides are subtracted and normalized by their sum (i.e., the background intensity) to produce a differential phase contrast image as shown in Eq. (1), $$I_{DPC} = \frac{I_L - I_R}{I_L + I_R} \quad (1)$$

where $I_L$ and $I_R$ represent the images with left and right illumination, respectively. Conventional, absorption-based contrast can be obtained by taking the sum of two opposite oblique illumination images.

In some embodiments, the one or more processors can be configured to construct a phase image of the sample based on the imaging data received. To extract quantitative phase from the collected differential phase contrast image, a transfer function for the imaging system as a whole can be found. While the formula for image formation in a microscope can be explained in terms of the propagation of mutual intensity, an equivalent description can be made in the context of angular spectra, which is more natural in the context of the presently disclosed illumination scheme. Thus, the measured intensity can be described by the illumination field $E(x)$ (with Fourier pair $E(u)$), with a distribution of illumination angles over u, the 2-dimensional angular coordinates, multiplied by the object transmittance function $o(x)$. This complex distribution can then be convolved with the pupil function of the system, and the amplitude squared is taken to yield the observed intensity. This can be expressed succinctly as, $$I(r) = |\mathcal{F}^{-1}(f)\mathcal{F}\{o(x)\mathcal{F}^{-1}\{E(u)\}\}|^2 \quad (2)$$

where $\mathcal{F}$ represents a 2D Fourier transform from spatial coordinates into spatial-frequency coordinates, x are the spatial coordinates at the focal plane, P(f) is the pupil function, either 0 or 1, in spatial frequency coordinates f that correspond to physical coordinates at the back focal plane, and r represents spatial coordinates at the camera. The coordinates u and f are both spatial frequency units, which map to units of propagation angle when scaled by a factor of λ. The coordinates x and r are in units of distance and correspond when scaled appropriately for magnification.

If the light source is incoherent, then Eq. (2) can be expressed as, $$I(r) = \int S(u)\left|\int P(f)\left[\int o(x)e^{i2\pi(f-u)\cdot x}d^2x\right]e^{i2\pi(f\cdot r)}d^2f\right|^2 d^2u \quad (3)$$

where $S(u)=|E(u)|^2$ is the corresponding angular intensity distribution from the scattering medium. In this form, the terms inside the modulus bracket indicate the equivalent intensity of an image formed when illuminated from a coherent source with a single incident angle u, and the outer integral indicates that the image formed from partial or fully incoherent illumination is the incoherent sum of images formed from contributing individual coherent plane waves.

Further, Eq. (3) demonstrates that the angular distribution of the source illumination intensity around the target gives sufficient information to produce a transfer function. In other words, the extent of spatial coherence of the microscope is fully determined by the breadth of the illumination intensity in angle space. This is beneficial for qOBM, as this quantity is readily available from photon transport simulation.

To extract the overall system transfer function from Eq. (3), some embodiments can expand the quantity within the modulus brackets using the identity $|\int f(m)\,dm|^2=\iint f(m)f^*(n)\,dm\,dn$. Substituting the variable m=f−u, and introducing the integration variable n, one of ordinary skill in the art can transform $o(x)$ to $O(m)$ and $O(n)$, and Eq. (3) becomes, $$I(r)=\iint O(m)O^*(n)C(m,n)\exp(i2\pi(r\cdot(m-n)))d^2m\,d^2n \quad (4)$$

where, $O(m)$ is the Fourier transform of the target object function $o(r)$, m and n are variables of integration in the spatial frequency space, and C is the transfer function of the microscope for a single image:

$$C(m,n)=\int S(u)P(m+u)P^*(n+u)d^2u \quad (5)$$

Here P is the pupil function of the system in u, the coordinates in the back focal plane of the microscope, and $S(u)$ represents the power spectrum in angular frequency of the illuminating light, or, proportionately, in illumination angle at the object. Equations (4) and (5) recapitulate the four-dimensional transfer function for a partially coherent microscope known in the art and in the literature from the Hopkins equation for mutual coherence. This demonstrates that the angular intensity distribution can provide sufficient information to determine the coherence of a system with an incoherent source, validating the use of illumination intensity angular spectra as a starting point for transfer function generation.

Equation (4) can be represented as a four-dimensional convolution with complex conjugate terms, a source of nonlinearity. This can be linearized with the assumption of a weak object. A thick sample may itself not be weakly scattering but scattering from outside of the focal plane can contribute to the angular intensity spectrum, so local phase effects outside of this region may not contribute to the image. The scattering of the object within the Rayleigh range is all that contributes to the reconstruction, and this can be said to be weak:

$$o(x) = \exp(-\mu(x) + i\phi(x)) \approx 1 - \mu(x) + i\phi(x) \quad (6)$$

where $\mu(x)$ and $\phi(x)$ are the (real valued) absorption and phase functions of the object. This means that the object function in the spatial frequency space is given by:

$$O(m) = \delta(m) - M(m) + i\Phi(m) \quad (7)$$

where M and $\Phi$ are Fourier transforms of $\mu$ and $\phi$, respectively. Expanding the product of the objects from Eq. (4), gives:

$$O(m)O^*(n) = \delta(m)\delta(n) - [M(m)\delta(n) + M^*(n)\delta(m)] + i[\Phi(m)\delta(n) - \Phi^*(n)\delta(m)] + \ldots \quad (8)$$

where the ellipses indicate cross terms that can be neglected as they are assumed to be small components of the weak phase. The delta functions in Eq. (8) serve to reduce the dimensions of the four-dimensional convolution to two dimensions when substituted in Eq. (4).

From the two-dimensional result, an optical transfer function can be derived to convert the DPC image to a phase image. The image that is produced in this way has phase gradient contrast, and the equivalent 2D optical phase transfer function is therefore given by, $$C_\Delta(m) = [\int S(u)P(m+u)P^*(u)d^2u - \int S(u')P(m+u')P^*(u')d^2u'] \quad (9)$$

where u' represents the coordinates in the back focal plane inverted in the shear direction: $u' = [-u_1, u_2]$, and the delta functions in Eq. (8) have allowed the setting of n=0 in Eq. (5). This transfer function is real and odd, therefore the point spread function given by its Fourier transform ($c_\delta(r)$) is purely imaginary. Hermitian symmetry ensures that an even source distribution gives rise to images that display absorption information, while an odd source distribution (synthesized here with the subtraction operation in Eq. (1)) gives phase information. Finally, the sum in the denominator of Eq. (1) normalizes the image by C(0, 0), a real-valued constant background term, and the DPC image can now be expressed as, $$I_{DPC}(r) = \mathcal{F}^{-1}\left\{ \frac{C_\Delta(m)}{C(0,0)} \cdot i\phi(m) \right\} \quad (11)$$
$$= \frac{\text{Im}\{c_\delta(r)\} * \phi(r)}{C(0,0)}$$

which directly yields access to the phase of the object.

In some embodiments, the one or more processors can be further configured to construct or deconvolute a QPI from the DPC image. From the distribution obtained from the photon transport simulation for a single LED source, an optical transfer function can be produced for the differential phase contrast (DPC) image formed by the microscope using Eq. (9), which can then be applied to recover the object function (Eq. (6)) with a deconvolution.

The formalism presented above only treats two sources to estimate the phase from a single DPC image which only carries information about refractive index variations along one direction (the direction between the two sources). Using a single shear direction to recover phase can lead to streak artifacts. To produce a fully quantitative phase image, the second pair of illumination sources is utilized, positioned orthogonally in horizontal angle to the first pair as shown in FIG. 1b. Then, the image of the ground truth object is reproduced with Tikhonov regularized deconvolution according to:

$$\phi = \mathcal{F}^{-1}\left\{ \frac{\sum_k \frac{\lambda_0}{\lambda_k} I_{DPC}^k C_{DPC}^*}{\sum_k |C_{DPC}|^2 + \alpha} \right\} \quad (12)$$

where $$C_{DPC} = \frac{iC_\Delta}{C(0,0)},$$

$\alpha$ is a regularization parameter, and the wavelength parameter $\lambda_k$ allows the phase displacement to be normalized to the corresponding phase of a single wavelength $\lambda_0$ (e.g., green $\lambda_0 = 530$ nm). Here k=2, corresponding to the two orthogonal DPC images. The result is a 2D quantitative tomographic phase image of an object embedded in a scattering medium. Combining the contributions from two orthogonal dimensions allows for features oriented in any direction to appear with equal contrast and produces an image that are both quantitative and superior in quality to those produced by either of the individual pairs of illuminations on their own.

The regularization parameter a can have a significant effect on the phase values in the images, so in order to ensure that an unbiased measure of phase could be obtained, an algorithm to arrive at the value automatically can be implemented. Although it affects both image quality and quantitative value, there is a theoretical optimal choice for a that maximizes smoothing of the image noise while minimizing the effect of causing a mismatch in the division operation in Eq. (12).

The regularization parameter was determined with generalized cross validation (GCV), as it requires no prior information about image or noise power. The GCV estimate of $\alpha$ is given in linear algebra formalism by:

$$\alpha = \text{argmin}\{V(\alpha)\} \quad (13)$$

where $$V(\alpha) = \frac{\|(Af - g)\|^2}{\text{Trace}[I - A(\alpha)]^2} \quad (14)$$

where A is a convolution matrix representation of the point spread function of the system, f is a solution for a given value of $\alpha$, g is the collected image data, I is the identity matrix, and $A(\alpha) = AA^*(AA^* + \alpha I)^{-1}$. Despite the recondite formalism, this approach has an intuitive explanation. The numerator in Eq. (14) represents the mean square error between the captured phase gradient image and the reconstructed phase gradient image. This reconstructed phase gradient can be produced by filtering the reconstructed quantitative phase object image through the system transfer function a second time, as if it were the original object being imaged. This reproduces a second phase gradient image similar to the one originally captured, only distorted slightly by having been processed a second time. The more similar the original captured phase gradient image is to the reprocessed one, the more faithfully the deconvolution procedure inverts the transfer function of the system. Therefore, minimizing this difference reduces the error introduced by the regularization parameter. The denominator in Eq. (14) represents the square sum deviation from unity when the forward transfer function of the system is deconvolved from itself, according to Eq. (12). This term mirrors the error in the numerator by analogy, but it serves to normalize the numerator by the amount of error the regularization parameter induces on the reprocessed transfer function itself. Images captured of different scenes with different ambient illumination intensity may alter the minimum value found with the numerator error term alone. The denominator term, then, ensures that the regularization parameter chosen is invariant with different images processed from the same modality. Because of this normalization term, this procedure can be performed once for a given imaging sample, rather than for each phase image. Alternatively, this procedure can be performed more than once for a given imaging sample, depending on desired resolution.

Figure 6B:
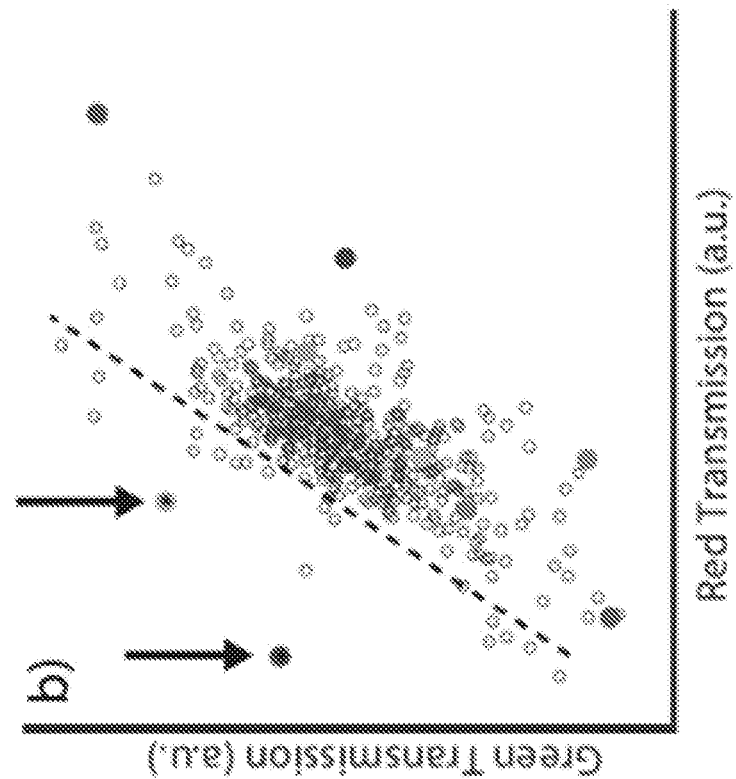
FIG. 6b shows a plot of transmission of light at a first and second frequency for a plurality of cells.
Figure 6A:
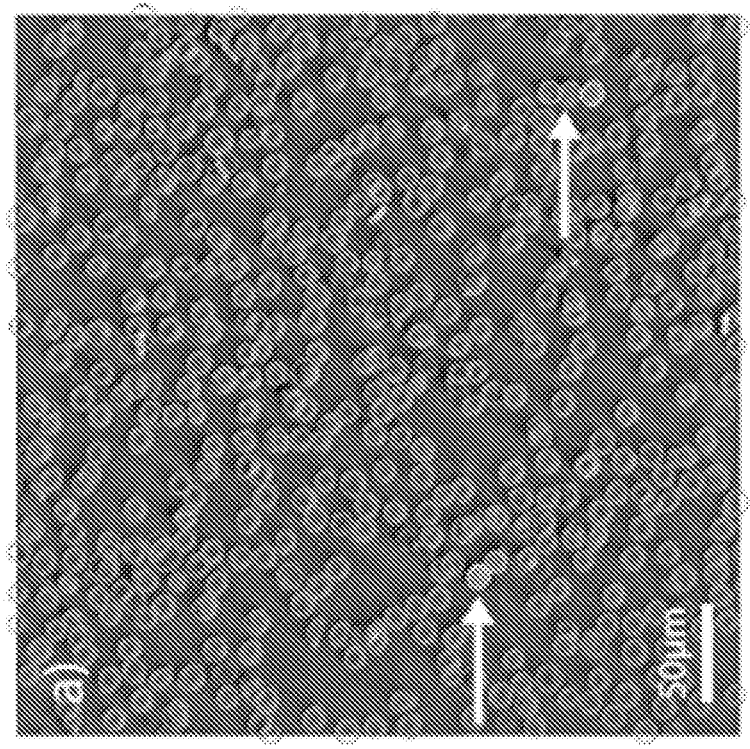
FIG. 6a shows an image produced by exemplary embodiments of a system for cell imaging and the methods of processing thereof.

In some embodiments, a sample plurality of cells can be characterized using the presently disclosed imaging system. Embodiments of the present disclosure can provide a quantitative phase image (QPI) of a plurality of cells. In some embodiments, a user of the system can analyze a plurality of cells for a desired cell. In such an embodiment, the system can be configured to receive a sample model of the desired cell from the user and cross-correlate the sample model with the QPI to compare each cell from the plurality of cells with the desired cell. The system can be further configured to indicate at least one cell from the plurality of cells is within a threshold similarity of, or similar to, the sample model. The system can then indicate that said at least one cell is a potential desired cell candidate, or a first desired cell candidate should there be one or more desired cell candidates. The system can indicate additional cells from the plurality of cells as desired cell candidates (e.g., a second desired cell candidate, a third desired cell candidate, etc.) as shown in FIG. 6a.

In some embodiments, light frequency absorption/transmission data can be received by the system from an objective image-capturing device. In some embodiments, the image-capturing device can be a camera, a flexible, or a rigid endoscope, or a fiber bundle to collect light frequency data. The light frequency data can comprise data regarding the frequency transmission of a plurality of cells. Said data may contain a distribution of light absorption data. In some embodiments, the system can be configured to calculate a relative or absolute value of light absorbed at a first and second frequency and compare the two absorptions. In some embodiments, cells from the plurality of cells falling outside a threshold standard deviation from the plurality of cells in the distribution can be indicated as desired cell candidates by the system. In some embodiments, the threshold standard deviation can be 1 or more (e.g., 1.5 or more, 2 or more, 2.5 or more, etc.). The system can then indicate that said at least one cell is a potential desired cell candidate, or a first desired cell candidate should there be one or more desired cell candidates. The system can indicate additional cells from the plurality of cells as desired cell candidates (e.g., a second desired cell candidate, a third desired cell candidate, etc.). An exemplary embodiment of a distribution of transmission data for a plurality of cells with indicated outliers is shown in FIG. 6b.

The system can further be configured to determine if there exists any overlap between the desired cell candidates from the QPI and the desired cell candidates from the absorption data. Should any cell from the plurality of cells be indicated as a desired cell by both the QPI and the absorption data, the system can indicate that cell as a desired cell. In some embodiments, the system can be configured to label the desired cell as a desired cell. Alternatively, the system can be configured to label a desired cell candidate as a false positive when the candidate only meets one of the desired cell criteria of the QPI or absorption data. Additionally, the system can provide a display of the image to a user of the system on a display with the corresponding labels.

Some embodiments of the present disclosure can provide a system for illuminating a sample to obtain images, imaging data, or light frequency absorption/transmission data. In some embodiments, the sample can be illuminated at for more frequencies (e.g., 2 or more, 3 or more, 4 or more). In such an embodiment, the illumination can be provided by 1 or more light sources (e.g., 2 or more, 3 or more, 4 or more, 5 or more, 6 or more). In some embodiments, the light sources can be provided in pairs and can be provided in 1 or more pairs (e.g., 2 or more pairs, 3 or more pairs, 4 or more pairs). In some embodiments, the light sources can be arranged such that an objective image capturing device is able to capture an illuminated image through epi-illumination as defined herein. In some embodiments, the light sources can comprise 1 or more light-emitting devices (e.g., 2 or more, 3 or more, 4 or more, 5 or more, 6 or more), such as light-emitting diodes (LEDs), optical fibers, fiber optic cables, incandescent lamps, and the like. In some embodiments, light from the light-emitting devices can be emitted at the same frequency. Alternatively, light can be emitted an any number of frequencies suitable to capture absorption data desired by one of ordinary skill in the art. Additionally, the light source can be positioned obliquely to the sample. In other embodiments, the light source can be positioned at any angle relative to the sample (e.g., 10 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, or 90 degrees). In some embodiments, multiple light sources can be position flanking an objective image-capturing device in an epi-illumination configuration. In such an embodiment, the oblique angle of the light sources can be selected such that the light sources on either side of the objective form an orthogonal angle with each other.

In some embodiments, the plurality of cells can be any living or once-living cells. For example, the plurality of cells can comprise blood cells, epithelial cells, cancer cells, stem cells, organoid cells, and the like. In some embodiments, the presently disclosed imaging systems and methods can be used beyond the application of a plurality of cells and used to image other structural features such as neurons, amyloid beta plaques, proteins, and the like.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

FIGS. 1a-1b and 2-4 illustrate exemplary embodiments of the presently disclosed systems and methods of imaging cells.

In FIGS. 1a-1b, a system for imaging cells is disclosed herein. As shown, a system 100 can be used to analyze a plurality of cells 110. The plurality of cells 110 can comprise any living or once-living cells. For example, the plurality of cells can comprise blood cells, epithelial cells, cancer cells, stem cells, organoid cells, and the like. In some embodiments, the presently disclosed imaging systems and methods can be used beyond the application of a plurality of cells and used to image other structural features such as neurons, amyloid beta plaques, proteins, and the like. The plurality of cells 110 can be imaged by an objective image-capturing device 130. For instance, the objective can comprise a lens or magnification and a camera for imaging. In some examples, the objective can be a microscope lens. The system 100 can further comprise light sources 121 and 122. Light sources 121 and 122 can be positioned on the same side of the plurality of cells 110 as the objective 130 in what is referred to herein as an epi-illumination configuration. As shown, light sources 121 and 122 can flank the objective 130 and can be positioned obliquely to the plurality of cells 110, such that the light sources 121 and 122 transmit light towards the plurality of cells 110 at oblique angles with respect to each other. Additionally, the light sources 121 and 122 can be positioned obliquely such that light source 121 forms an orthogonal angle with light source 122. In some examples, the system can comprise a first light source 121 and a second light source 122. Each light source can comprise a pair of light-emitting devices. Alternatively, each light source can comprise two or more light-emitting devices. In some embodiments, each light source can comprise one or more light-emitting devices. The light-emitting devices can comprise LEDs, optical fibers, fiber optic cables, incandescent lamps, halogen light bulbs, and the like.

Figure 2:
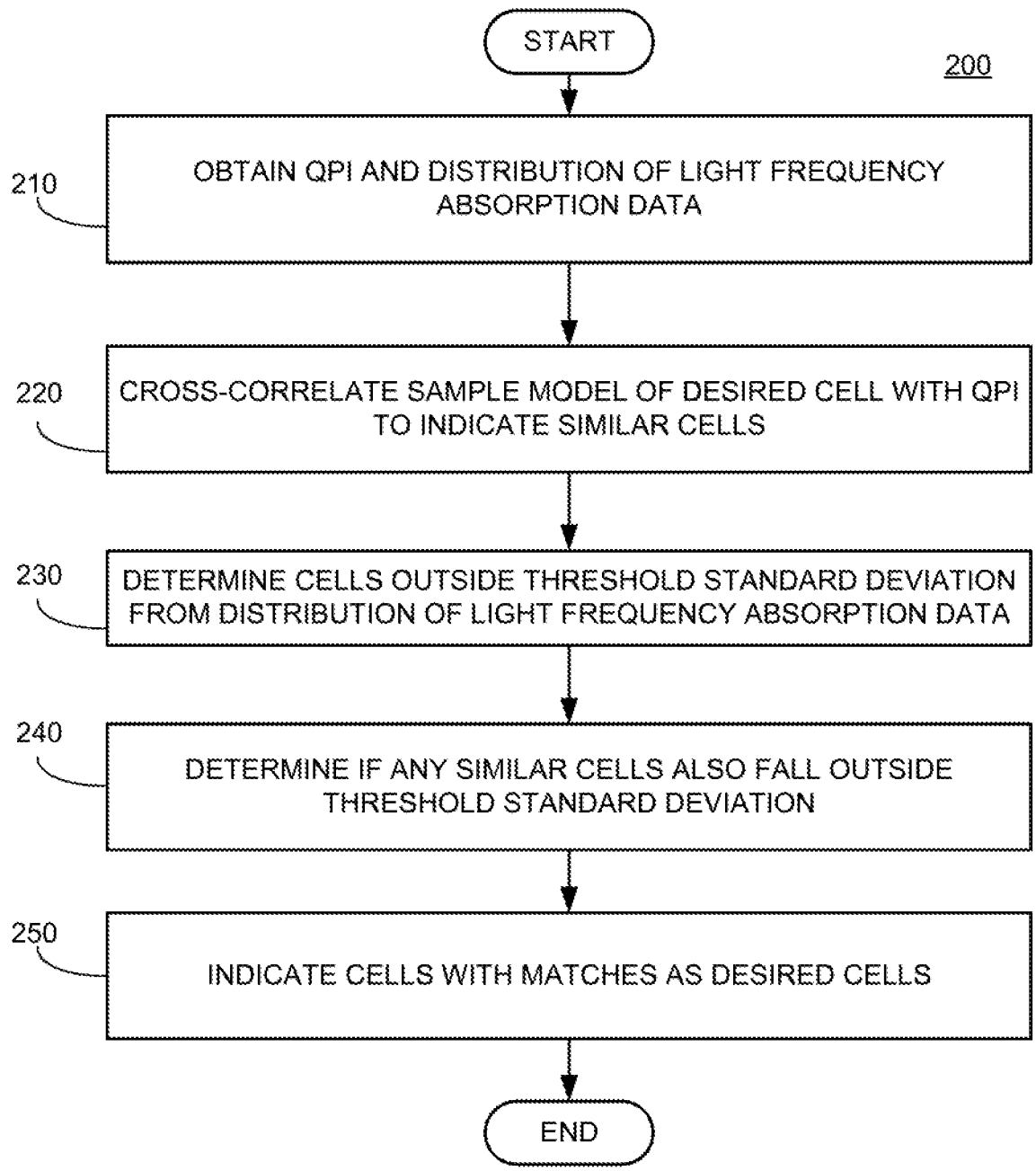
FIG. 2 is a flowchart of an exemplary method for imaging cells.

In FIG. 2, a method 200 for imaging cells is disclosed herein. In block 210, a quantitative phase image (QPI) can be obtained along with light frequency absorption/transmission data for a plurality of cells being imaged. In block 220, the QPI can be cross-correlated with a sample model of a desired cell. For example, if a white blood cell is the desired cell to be imaged, a sample model of a white blood cell can be provided and cross-correlated with the QPI. Additionally, cells determined to be similar to the sample model are indicated as such. For example, a cell similar to the sample model can be indicated as a first desired cell candidate. In block 230, the light frequency absorption data can be used to determine outliers from the plurality of cells. For instance, the plurality of cells can produce a normal distribution of light absorption at a given frequency. Cells found to lie outside a threshold standard deviation, such as 1.5 standard deviations, are indicated to be outliers. Additionally, the outliers can be indicated as potential desired cells. For example, a cell having a light frequency absorption greater than 1.5 standard deviations can be indicated as a second desired cell candidate. In block 240, the first and second desired cell candidates can be analyzed to determine if they are the same cell. In other words, cells which match the sample model and are outliers to the light absorption data are indicated as desired cells. Cells which only meet one of the criteria can be indicated as false positives. In block 250, the desired cells can be indicated as such.

Figure 3:
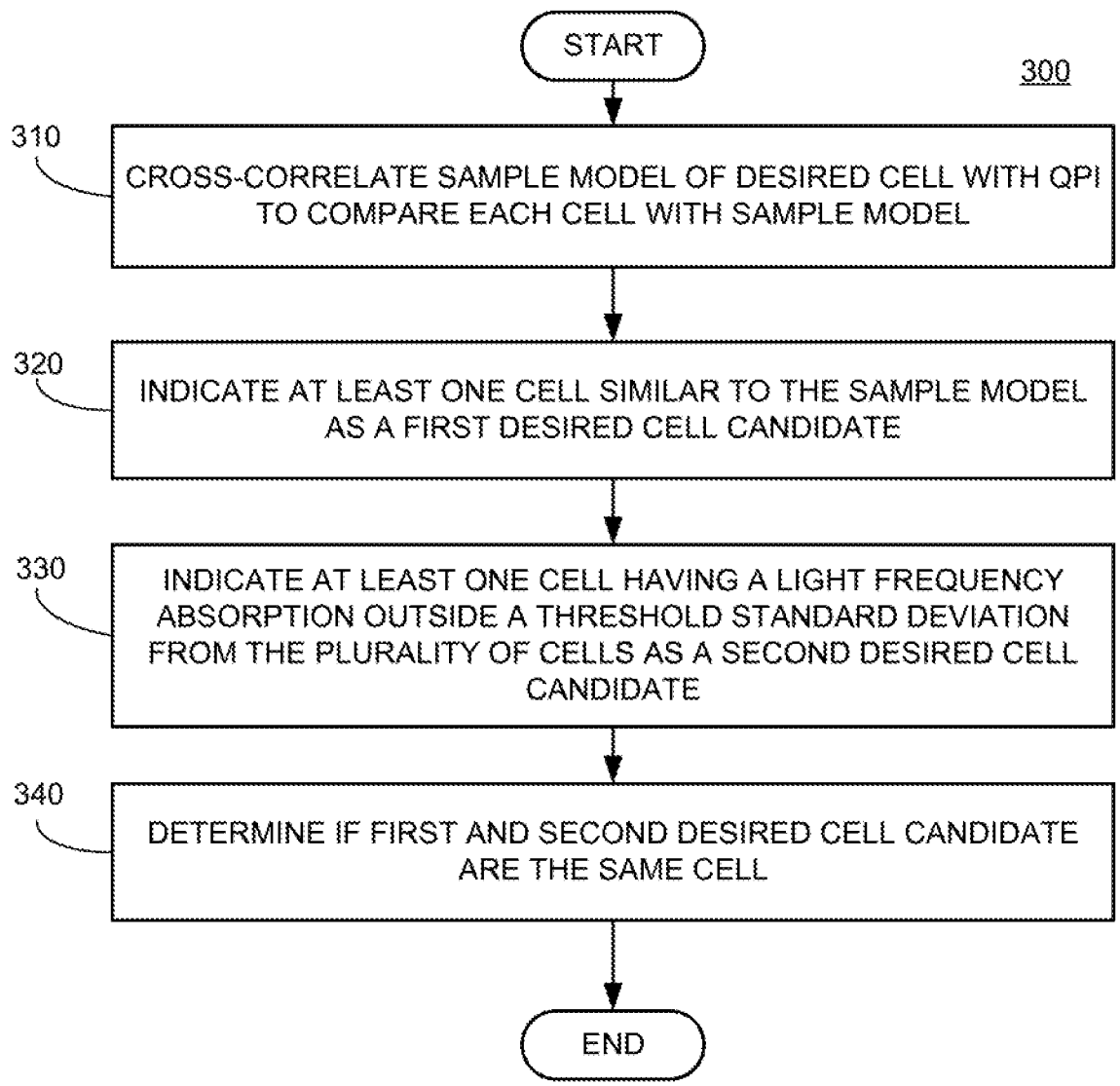
FIG. 3 is a flowchart of an exemplary method for imaging cells.

In FIG. 3, a method 300 for imaging cells is disclosed herein. In block 310, the QPI can be cross-correlated with a sample model of a desired cell. For example, if a white blood cell is the desired cell to be imaged, a sample model of a white blood cell can be provided and cross-correlated with the QPI. Additionally, cells determined to be similar to the sample model are indicated as such in block 320. For example, a cell similar to the sample model can be indicated as a first desired cell candidate. In block 330, the light frequency absorption data can be used to determine outliers from the plurality of cells. For instance, the plurality of cells can produce a normal distribution of light absorption at a given frequency. Cells found to lie outside a threshold standard deviation, such as 1.5 standard deviations, are indicated to be outliers. Additionally, the outliers can be indicated as potential desired cells. For example, a cell having a light frequency absorption greater than 1.5 standard deviations can be indicated as a second desired cell candidate. In block 340, the first and second desired cell candidates can be analyzed to determine if they are the same cell. In other words, cells which match the sample model and are outliers to the light absorption data are indicated as desired cells. Cells which only meet one of the criteria can be indicated as false positives.

Figure 4:
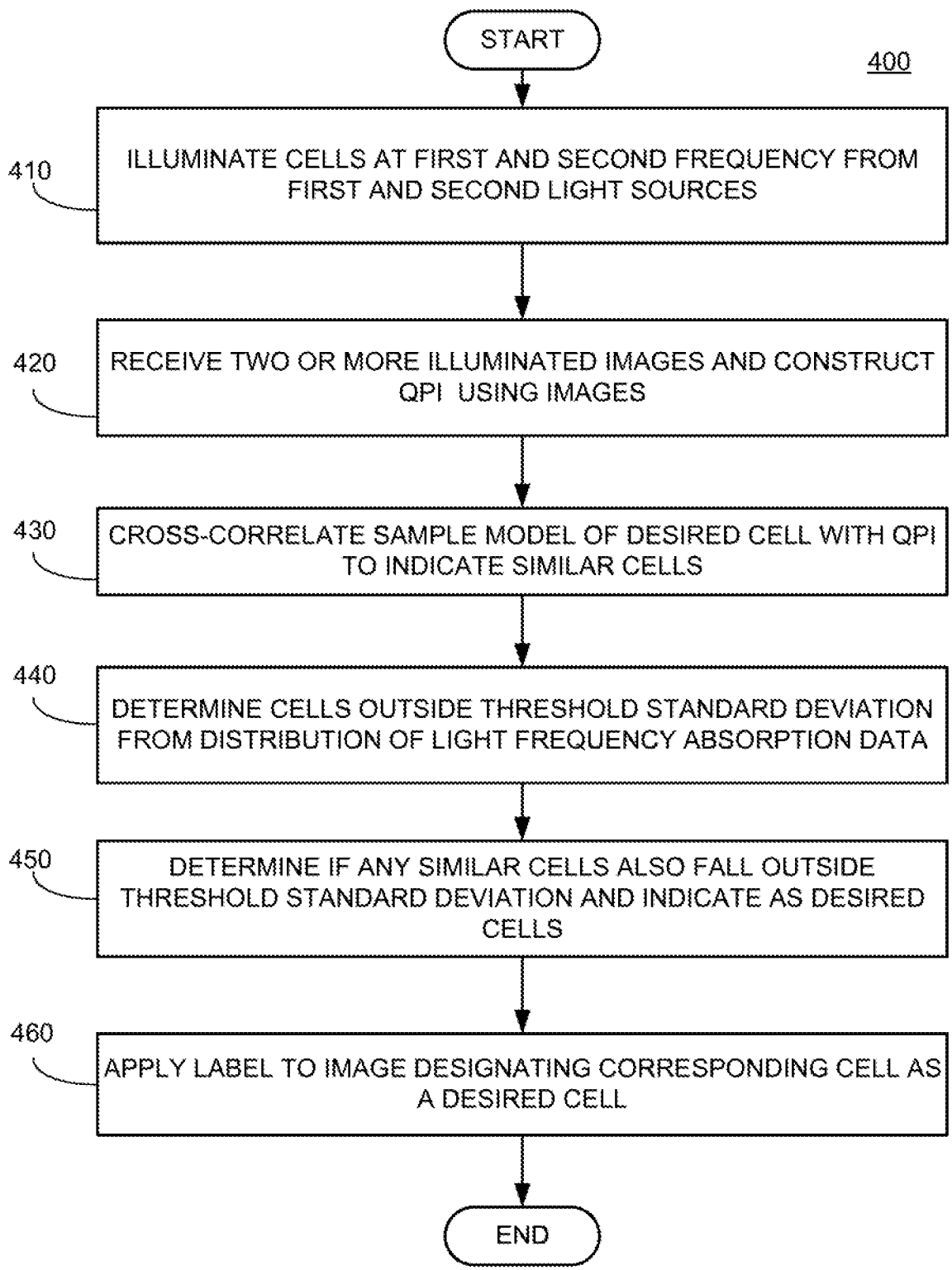
FIG. 4 is a flowchart of an exemplary method for imaging cells.
Figure 5:
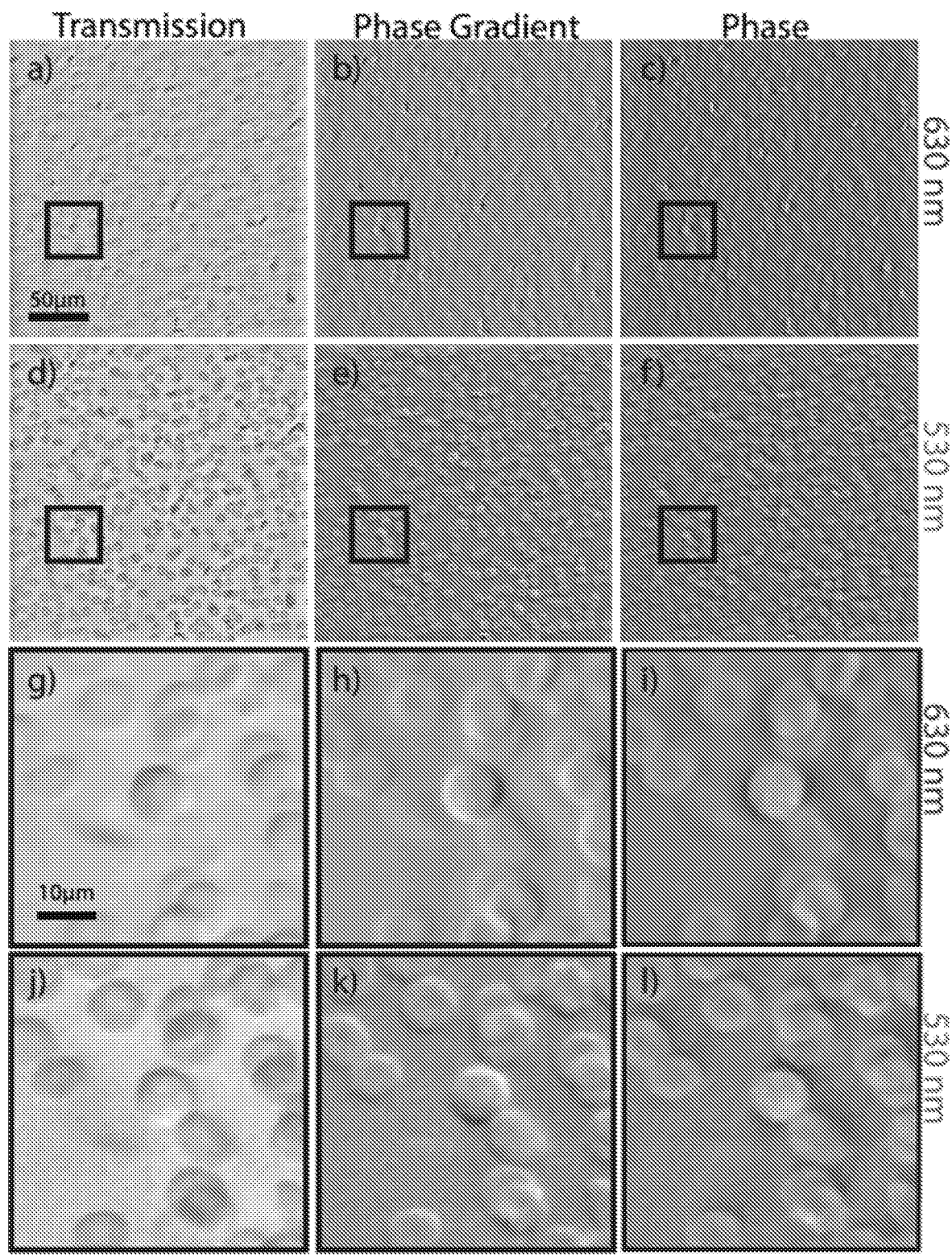
FIG. 5 shows images produced by exemplary embodiments of a system for cell imaging and the methods of processing thereof.

In FIG. 4, a method 400 for imaging cells is disclosed herein. In block 410, the sample can be illuminated by the first and second light sources at a first and second frequency. In block 420, two or more illuminated images of the sample can be received, and the QPI can be constructed using the methods disclosed herein. In block 430, the QPI can be cross-correlated with a sample model of a desired cell. For example, if a white blood cell is the desired cell to be imaged, a sample model of a white blood cell can be provided and cross-correlated with the QPI. Additionally, cells determined to be similar to the sample model are indicated as such. For example, a cell similar to the sample model can be indicated as a first desired cell candidate. In block 440, the light frequency absorption data can be used to determine outliers from the plurality of cells. For instance, the plurality of cells can produce a normal distribution of light absorption at a given frequency. Cells found to lie outside a threshold standard deviation, such as 1.5 standard deviations, are indicated to be outliers. Additionally, the outliers can be indicated as potential desired cells. For example, a cell having a light frequency absorption greater than 1.5 standard deviations can be indicated as a second desired cell candidate. In block 450, the first and second desired cell candidates can be analyzed to determine if they are the same cell. In other words, cells which match the sample model and are outliers to the light absorption data are indicated as desired cells. Cells which only meet one of the criteria can be indicated as false positives. In block 460, the desired cells can be indicated as such and labelled in an image as desired cells.

Figure 10:
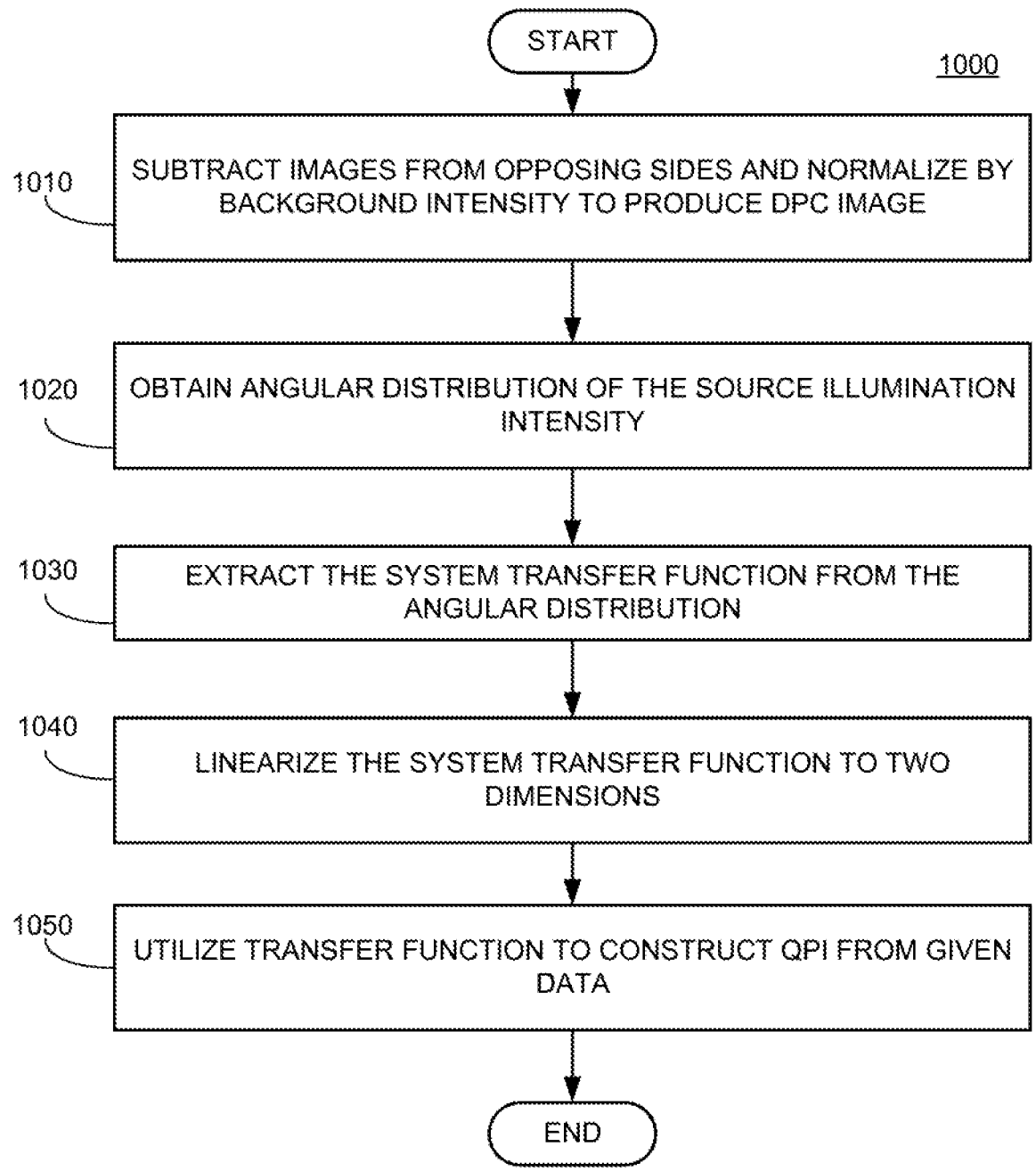
FIG. 10 is a flowchart of an exemplary method for the construction of a quantitative phase image for use in the presently disclosed method for imaging cells.

In FIG. 10, a method for constructing a Quantitative Phase Image (QPI) is described herein. In block 1010, two or more images (e.g., three or more, four or more, five or more) from different angles relative to the sample can be subtracted from one another and normalized to produce a differential phase contrast image. In block 1020, the angular distribution of illumination intensity can be obtained using the methods as described herein. In block 1030, the system transfer function can be extracted from the angular distribution. In block 1040, the system transfer function can be linearized to two dimensions. In block 1050, the two-dimensional transfer function can be used to construct a QPI from the given data using the methods as described herein.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

EXAMPLES

The following examples are provided by way of illustration but not by way of limitation.

Example 1

Materials

In an assembly of a system for imaging cells, four LEDs (Luxeon sink-PAD II) are coupled into multimode plastic fibers (Thorlabs FP1000ERT, numerical aperture (NA) 0.5, 1000 μm diameter), each using an aspheric condenser lens (Thorlabs ACL2520U-A, NA 0.6). These fibers are housed in a custom 3D printed objective adapter which holds them at the desired incident angle and off-axis source-detector distance. From previous experiments, the system currently uses two sets of colored LEDs, one at 530 nm (green), and another 630 nm (red), selected to provide absorption spectral information key to performing blood cell classification. Different wavelengths can be used to optimize for a specific task. Imaging was performed on an inverted microscope (Zeiss Axiovert 200) with a 60× objective, (Nikon S Plan ELWD, NA 0.7), at a resolution of 0.6 pm. The LEDs illuminate the sample individually, and light is detected with a digital camera (sCMOS pco.eddge 42LT) at 20 Hz. The illumination and camera triggering were coordinated with custom software (National Instruments LabVIEW 2017) and a data acquisition block (National Instruments SCB-68A).

Example 2

Materials and Methods

Human blood was drawn from consenting human donors by vasopuncture into heparinized tubes and diluted with phosphate-buffered saline (PBS) to 1% of pure blood concentration. All procedures adhered to approved Institutional Review Board protocols. The blood was transferred into custom-made translucent PVC bag (InstantSystems) and placed on a glass slide over the objective to flatten the bag and reduce bowing. The objective lens was focused on cells from the blood bag suspension that had settled on the inner surface of the bag, which were illuminated by the diffuse scattering of the LED light from the fibers. Imaging from this constant plane provided a consistent cross-section of the cells in the image and reduced motion artifacts. Also, the dual wavelength configuration yields spectral information from the absorption images to distinguish white from red blood cells.

Figure 7:
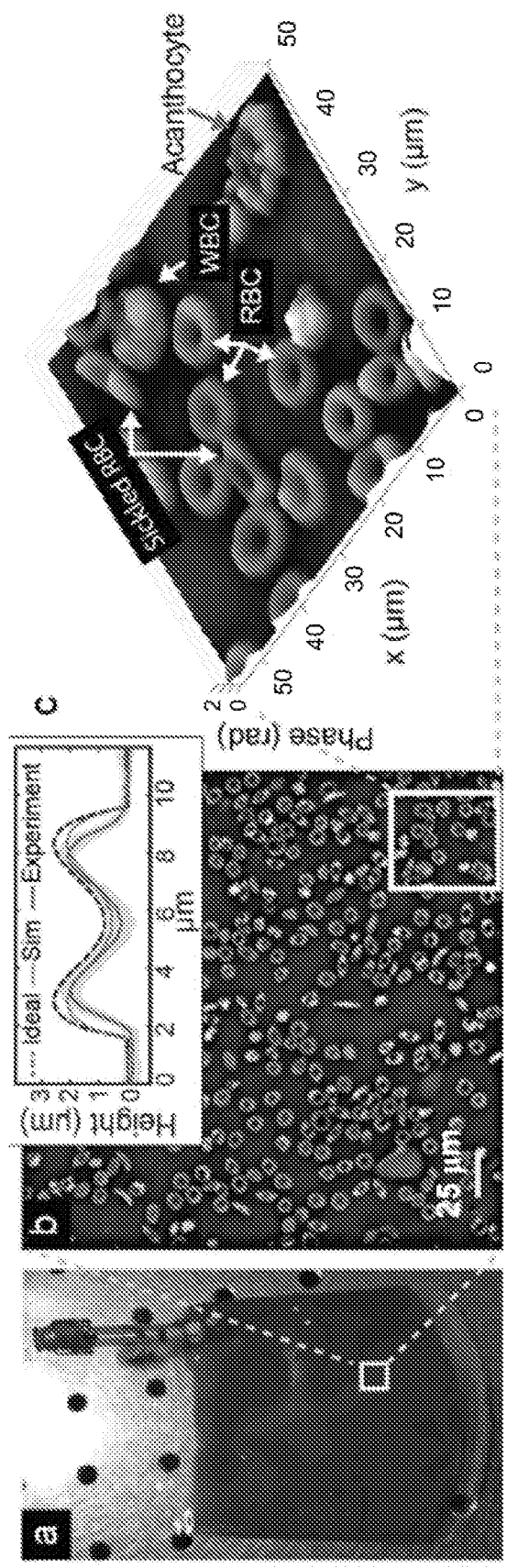
FIG. 7 shows reconstructed images of a plurality of cells obtained from the presently disclosed system and method.

FIG. 7 shows representative results, where the quantitative phase images show remarkable details of gross cellular morphology and sub-cellular features. Here one can clearly see normal biconcave and sickled RBCs, acanthocytes, and white blood cells along with their internal contents, including the nucleus. In addition to extracting feature-rich morphology, qOBM maintains a reliable quantitative phase profile. A cross section of 20 biconcave red blood cells from the displayed image is compared with an ideal standard theoretical healthy cell profile and the numerical simulation thereof. Again, the results show excellent agreement.

Example 3

Materials and Methods

Next, the present disclosure was used to image whole mouse brains. All animal experimental protocols were approved by Institutional Animal Care and Use Committee (IACUC) of the Georgia Institute of Technology. The mice (*Mus musculus*) used were of a C57/BL6 genetic background and were 14 months old. Whole brains were dissected, briefly rinsed in phosphate buffered saline and then placed directly on a microscope slide for imaging without staining, slicing or other alteration unless otherwise specified in the corresponding image caption.

All images were collected at 20 Hz, limited by the signal-to-noise ratio of the image from the intensity of scattered illumination light impinging on the object at the focal plane. As the inverse transfer function is produced before-hand for a given scattering medium geometry, quantitative phase images are computed and displayed in real-time, facilitating the task of finding and identifying structures and landmarks.

Figure 8:
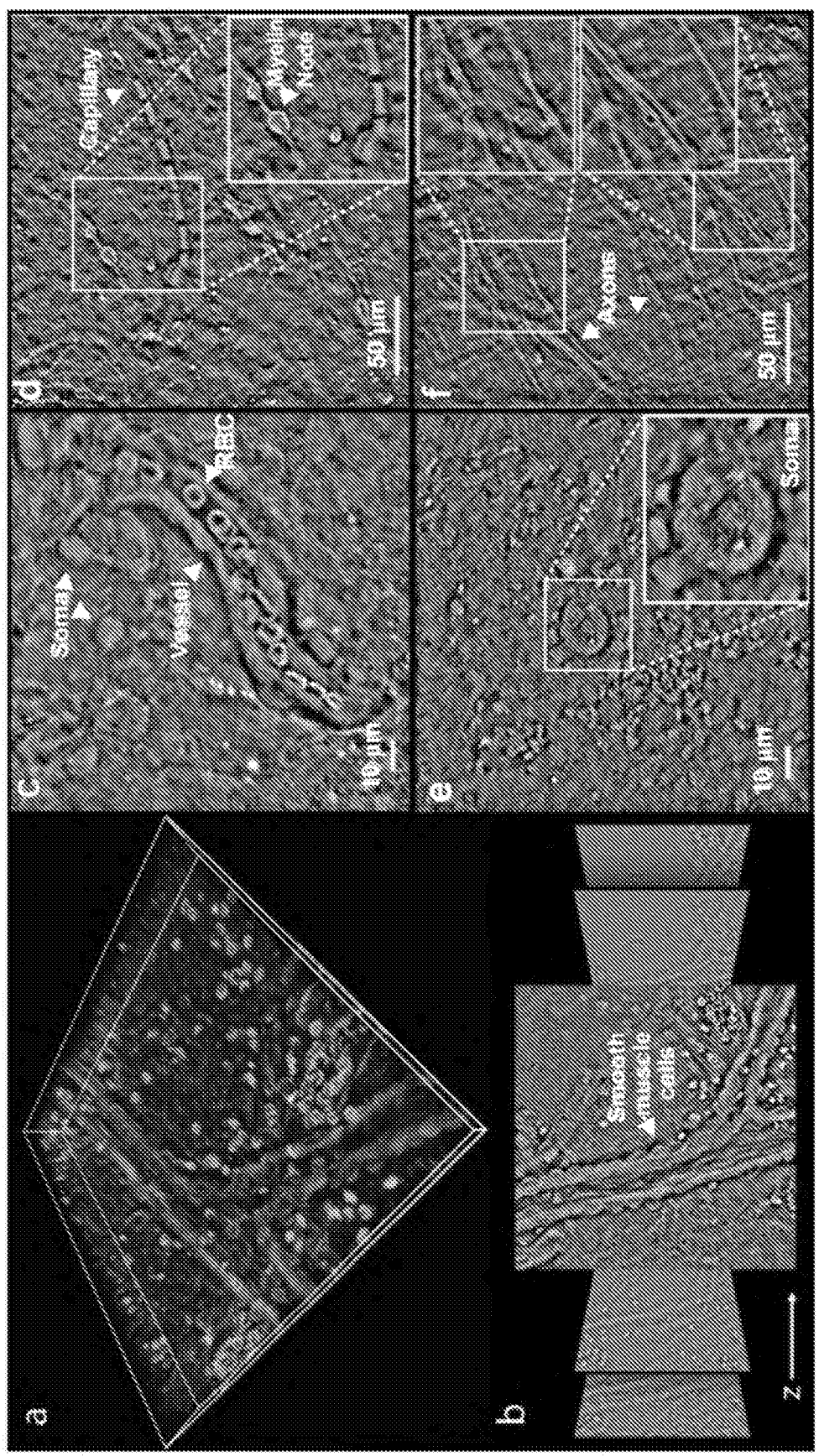
FIG. 8 shows reconstructed images of a plurality of cells obtained from the presently disclosed system and method.

FIG. 8 shows the results. Here fine structural details can clearly be observed, such as neural cell soma with resolvable internal cell contents, smooth muscle cells, blood vessels and nearby glial cells. From coronal sections, axons as well as cell bodies of neurons and glia were able to be resolved. To demonstrate this optical sectioning capability, 100 images were captured in a z-stack (0.6 μm steps), centered on a blood vessel in the cortex. The maximum intensity projection of the 3D volume clearly shows the vessel, red blood cells, and tissue structures.

Example 4

Materials and Methods

Figure 9:
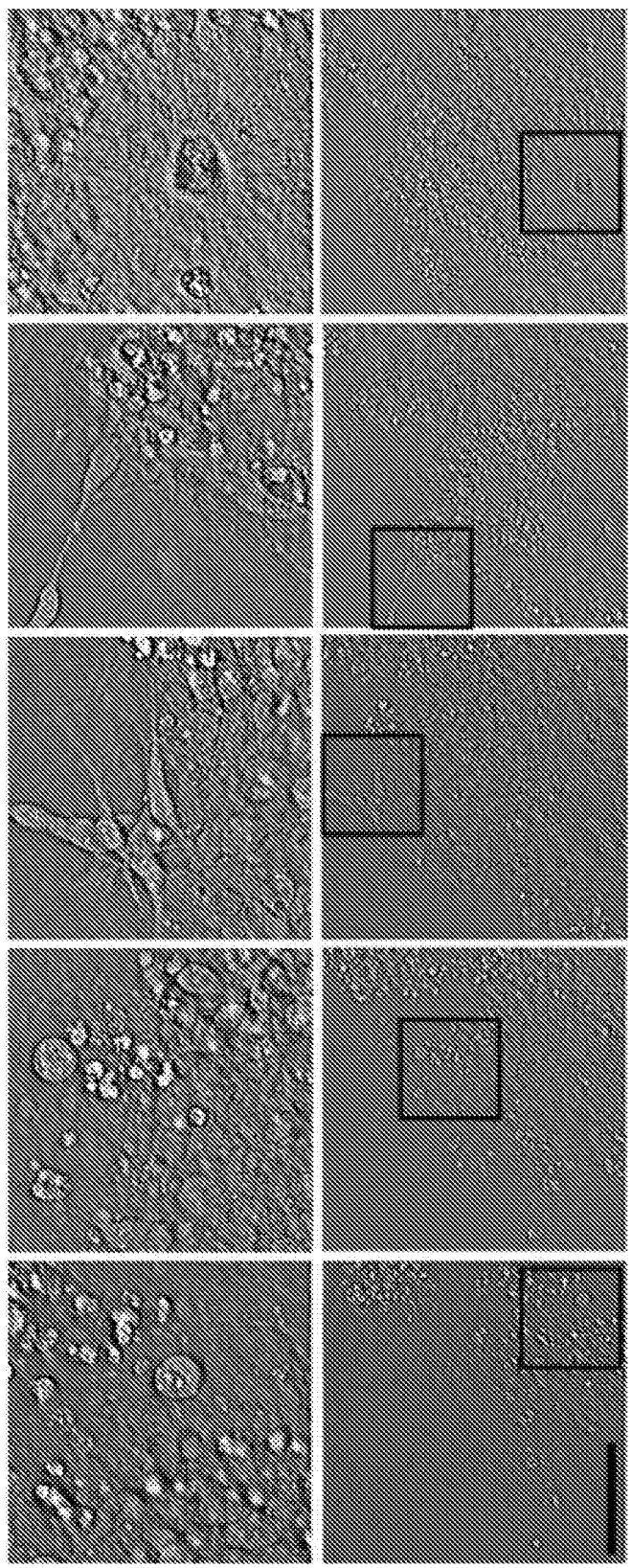
FIG. 9 shows reconstructed images of a plurality of cells obtained from the presently disclosed system and method.

Finally, the present disclosure was used to image cerebral organoids. Organoids are cell-derived 3D organ models that mimic the structure and cell diversity of native biological tissue and have rapidly emerged as powerful in vitro model of diseases that are intractable or impractical to study in humans or animal models. Organoids are typically grown and incubated in enclosed bioreactors, wherein non-invasive live imaging of growth and organization of developing heterogeneous tissue could facilitate an understanding of, for example, complex developmental diseases, such as Autism Spectrum Disorder and microencephaly. FIG. 9 shows a series of qOBM images of a 26-day old cerebral organoid taken at various depths with 10 μm increments. Notable features include neuroblasts and immature neurons, mature neurons with sub-cellular detail, neural progenitor cells, and the characteristic "rosette" shape formed by neural progenitor cells that develop and grow radially. These images show qOBM's unique potential to monitor the structure, growth, and health of organoids without labels.

While the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. A method comprising:
   cross-correlating a sample model of a desired cell with a quantitative phase image of cells to compare cells of the quantitative phase image with the sample model of the desired cell;

indicating a cell from the cells similar to the sample model as a first desired cell candidate;

indicating a cell from the cells having a light frequency absorption outside of a threshold standard deviation from the cells as a second desired cell candidate; and determining, based on the quantitative phase image of cells and a distribution of light frequency absorption data for the cells, if the first desired cell candidate and the second desired cell candidate are the same cell.

2. The method of claim 1, wherein the distribution of light frequency absorption data for the cells is obtained by:
illuminating the cells with light at a first frequency;
illuminating the cells with light at a second frequency; and
receiving two or more illuminated images of the cells.

3. The method of claim 2 further comprising comparing a value of light absorbed at the first frequency to light absorbed at the second frequency for one or more of the cells.

4. The method of claim 2 further comprising constructing a phase gradient image by subtracting an illuminated image at the second frequency from an illuminated image at the first frequency.

5. The method of claim 2 further comprising constructing an absorption contrast image by adding two or more illuminated images together.

6. The method of claim 2, wherein illuminating comprises:
emitting light at the first frequency from a first pair of light sources;
emitting light at the second frequency from a second pair of light sources;
wherein the first and second pairs of light sources and an objective lens are on a same side of the cells; and
wherein the first and second pairs of light sources are configured to transmit light obliquely to the cells.

7. The method of claim 6, wherein the first and second pair of light sources comprise two or more light-emitting devices.

8. The method of claim 7, wherein the two or more light-emitting devices comprise light-emitting diodes (LEDs).

9. The method of claim 7, wherein a first and a second light-emitting device are positioned flanking the objective lens, such that each of the first and second pair of light sources comprise a first and a second light-emitting device on either side of the objective lens.

10. The method of claim 9, wherein the first and the second light-emitting devices on either side of the objective lens form an orthogonal angle with each other, such that each of the first and second pair of light sources comprise a first and a second light-emitting device on either side of the objective lens and forming an orthogonal angle.

11. The method of claim 7, wherein the two or more light-emitting devices comprise fiber optic cables.

12. The method of claim 1 further comprising labelling as a desired cell the cell when the first desired cell candidate and the second desired cell candidate are the same cell.

13. The method of claim 1 further comprising labelling as a false positive the cell when the first desired cell candidate and the second desired cell candidate are not the same cell.

14. The method of claim 1, wherein indicating the cell having the light frequency absorption outside of the threshold standard deviation from the cells comprises:
illuminating the cells with light at a first frequency;
illuminating the cells with light at a second frequency;
calculating a ratio of light absorbed at the first frequency to light absorbed at the second frequency for one or more of the cells; and
determining which cells have a ratio of light absorbed outside the threshold standard deviation value from the cells.

15. A method comprising:
illuminating a plurality of cells with light at a first frequency from a first light source;
illuminating the plurality of cells with light at a second frequency from a second light source;
receiving illuminated images of the plurality of cells at an objective;
constructing a quantitative phase image from the illuminated images;
cross-correlating a sample model of a desired cell with the quantitative phase image to compare one or more cell from the plurality of cells with the desired cell;
indicating at least one cell from the plurality of cells similar to the sample model as a first desired cell candidate;
indicating at least one cell from the plurality of cells having a light frequency absorption ratio outside of a threshold standard deviation from the plurality of cells as a second desired cell candidate;
determining, based on the quantitative phase image and a distribution of light frequency absorption data, if the first desired cell candidate and the second desired cell candidate are the same cell; and
labelling the cell corresponding to the first and the second desired cell candidate as a desired cell, responsive to determining that the first and second desired cell candidates are the same cell.

16. A method of imaging cell samples comprising:
cross-correlating a sample model of a desired cell with a quantitative phase image to compare each cell from a plurality of cells with the desired cell;
indicating at least one cell from the plurality of cells similar to the sample model as a first desired cell candidate;
indicating at least one cell from the plurality of cells having a light frequency absorption outside of a threshold standard deviation from the plurality of cells as a second desired cell candidate; and
determining, based on the quantitative phase image and the distribution of light frequency absorption data, if the first desired cell candidate and the second desired cell candidate are the same cell.

17. The method of claim 16 further comprising:
obtaining a distribution of light frequency absorption data by:
illuminating the plurality of cells with light at a first frequency;
illuminating the plurality of cells with light at a second frequency; and
receiving two or more illuminated image of the plurality of cells at an objective.

18. The method of claim 17 further comprising calculating a ratio of light absorbed at the first frequency to light absorbed at the second frequency for each cell from the plurality of cells.

19. The method of claim 17 further comprising constructing a phase gradient image by subtracting an illuminated image at the second frequency from an illuminated image at the first frequency.

20. The method of claim 17 further comprising constructing an absorption contrast image by adding the two or more illuminated images together.

21. A system for imaging of cells, comprising:
a first and a second light source, each of the first and second light source comprising two or more light-emitting devices;
an objective image-capturing device;
a display;
a processor; and
at least one memory storing instructions that when executed by the processor, cause the system to:
receive imaging data from the objective image-capturing device, the imaging data comprising light frequency absorption data for a plurality of cells;
construct, using the light frequency absorption data, a quantitative phase image of the plurality of cells;
cross-correlate a sample model of a desired cell with the quantitative phase image to compare each cell from the plurality of cells with the sample model of the desired cell;
indicate at least one cell from the plurality of cells similar to the sample model as a first desired cell candidate;
indicate at least one cell from the plurality of cells having a light frequency absorption outside of a threshold standard deviation from the plurality of cells as a second desired cell candidate; and
determine, based on the quantitative phase image and the distribution of light frequency absorption data, if the first desired cell candidate and the second desired cell candidate are the same cell.

22. A system for imaging of cells, comprising:
a first and a second light source, each of the first and second light source comprising two or more light-emitting devices and configured to illuminate a plurality of cells;
an objective image-capturing device;
a plurality of cells;
a processor; and
memory storing instructions that, when executed by the processor, cause the system to:
receive imaging data from the objective image-capturing device, the imaging data comprising light frequency absorption data for a plurality of cells;
construct, using the light frequency absorption data, a quantitative phase image of the plurality of cells;
cross-correlate a sample model of a desired cell with the quantitative phase image to compare each cell from the plurality of cells with the desired cell;
indicate at least one cell from the plurality of cells similar to the sample model as a first desired cell candidate;
indicate at least one cell from the plurality of cells having a light frequency absorption outside of a threshold standard deviation from the plurality of cells as a second desired cell candidate;
wherein the first and second light sources are on the same side of the plurality of cells as the objective and are configured to transmit light obliquely to the plurality of cells;
wherein a first and a second light-emitting device from the two or more light-emitting devices are positioned flanking the objective, such that each of the first and second light sources comprise a first and a second light-emitting device on either side of the objective; and
wherein the first and the second light-emitting devices on either side of the objective form an orthogonal angle with each other, such that each of the first and second light sources comprise a first and a second light-emitting device on either side of the objective and forming an orthogonal angle.

* * * * *